(12) United States Patent
Melzner et al.

(10) Patent No.: US 9,891,230 B2
(45) Date of Patent: Feb. 13, 2018

(54) MICROARRAY DEVICE FOR SCREENING OR LOCATING HSP90 INHIBITORS OR INHIBITORS OF FURTHER DISEASE-RELEVANT TARGET STRUCTURES

(75) Inventors: Dieter Melzner, Gottingen (DE); Thomas Scheper, Hannover (DE); Thomas Schueler, Jena (DE); Frank Stahl, Hannover (DE); Denise Van Rossum, Adelebsen (DE); Johanna-Gabriela Walter, Nienburg (DE); Carsten Zeilinger, Hannover (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 1074 days.

(21) Appl. No.: 14/128,298

(22) PCT Filed: Apr. 20, 2012

(86) PCT No.: PCT/EP2012/001725
§ 371 (c)(1),
(2), (4) Date: Apr. 16, 2014

(87) PCT Pub. No.: WO2013/007324
PCT Pub. Date: Jan. 17, 2013

(65) Prior Publication Data
US 2014/0228235 A1    Aug. 14, 2014

(30) Foreign Application Priority Data
Jul. 8, 2011 (DE) .................. 10 2011 106 984

(51) Int. Cl.
  *G01N 33/543* (2006.01)
  *G01N 33/68* (2006.01)
(52) U.S. Cl.
  CPC ..... *G01N 33/6845* (2013.01); *G01N 33/6872* (2013.01)
(58) Field of Classification Search
  None
  See application file for complete search history.

(56) References Cited

U.S. PATENT DOCUMENTS

| | | | | |
|---|---|---|---|---|
| 6,777,190 B1* | 8/2004 | Buechler | ............ | C07D 207/416 424/178.1 |
| 8,158,376 B2* | 4/2012 | Uri | .................. | A61K 47/48315 435/15 |
| 2004/0005582 A1* | 1/2004 | Shipwash | ........ | G01N 33/54366 435/6.19 |
| 2004/0204586 A1* | 10/2004 | Sircar | .................. | A61K 31/496 544/363 |
| 2005/0112701 A1* | 5/2005 | Arndt | ................. | G01N 33/6893 435/7.2 |
| 2005/0208539 A1* | 9/2005 | Vann | .................. | B01L 3/502707 435/6.11 |
| 2007/0105874 A1* | 5/2007 | Zhang | .................. | A61K 31/519 514/259.3 |
| 2008/0200488 A1* | 8/2008 | Manley | ................ | A61K 31/365 514/275 |
| 2008/0261829 A1* | 10/2008 | Harvey | ................ | G01N 33/574 506/13 |
| 2009/0092966 A1* | 4/2009 | Anderson | .............. | B82Y 30/00 435/6.12 |

FOREIGN PATENT DOCUMENTS

| | | |
|---|---|---|
| EP | 2 226 632 A1 | 9/2010 |
| WO | 03/050295 A2 | 6/2003 |
| WO | WO 03/050295    * | 6/2003 |
| WO | 2005/012482 A2 | 2/2005 |

OTHER PUBLICATIONS

J. Kim et al; "Development of a fluorescence polarization assay for the molecular chaperone Hsp90", Journal of Biomolecular Screening, vol. 9, No. 5, Aug. 1, 2004; pp. 375-381.
International Search Report PCT/EP2012/001725 dated Oct. 7, 2012.

* cited by examiner

*Primary Examiner* — Ann Lam
(74) *Attorney, Agent, or Firm* — McDonald Hopkins LLC

(57) ABSTRACT

The present invention relates to a microarray device for the screening or the finding of protein inhibitors, to a method for the production thereof, and to a corresponding method for screening or finding protein inhibitors. The microarray device according to the invention comprises a solid supporting element having a support material, at least one protein immobilized thereon for which inhibitors are to be screened or found, and at least one known inhibitor of the at least one protein, the inhibitor being bound to the at least one protein and comprising a detectable label.

14 Claims, 3 Drawing Sheets

Figure 1:
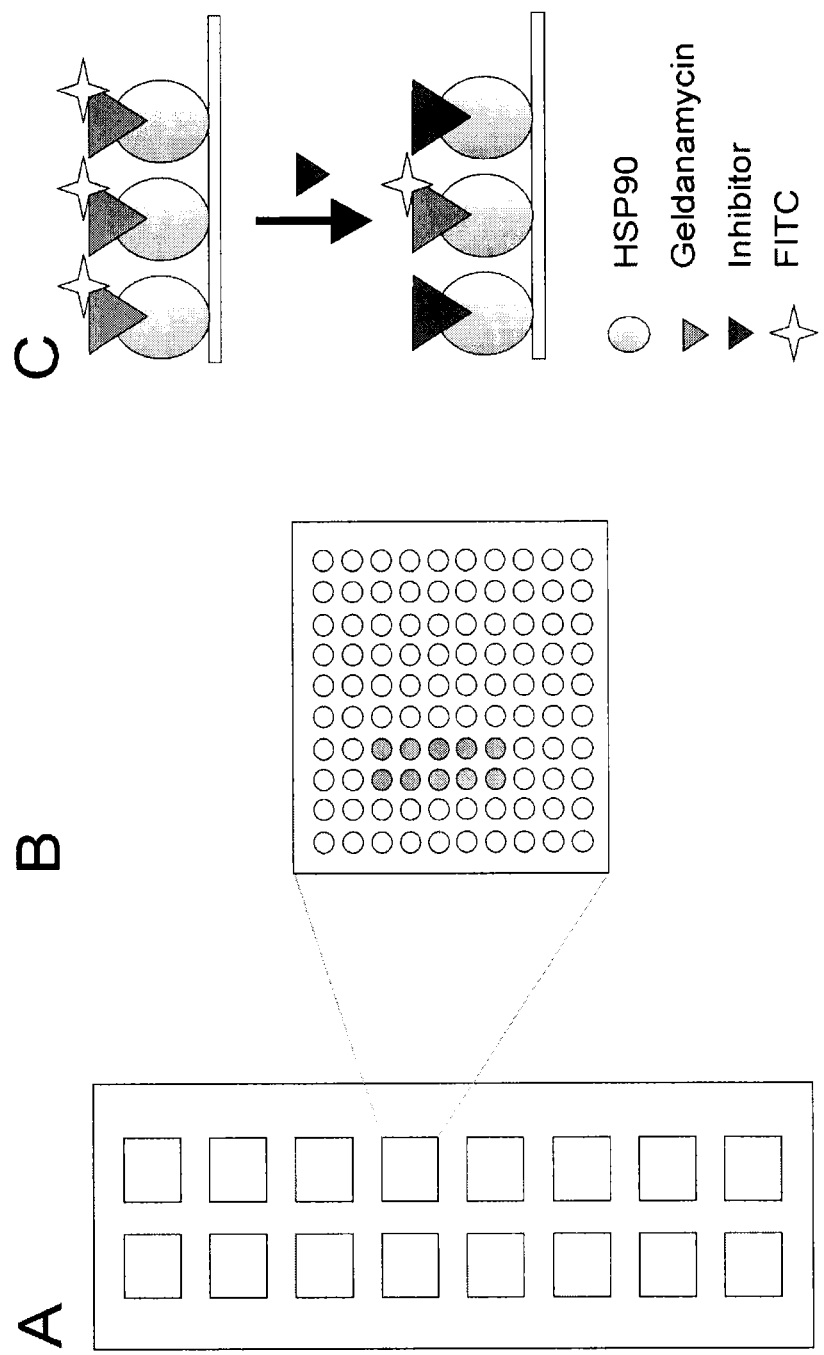

MICROARRAY DEVICE FOR SCREENING OR LOCATING HSP90 INHIBITORS OR INHIBITORS OF FURTHER DISEASE-RELEVANT TARGET STRUCTURES

This application claims priority to PCT Application No. PCT/EP/2012/001725, entitled "Microarray device for the screening or finding of HSP90 inhibitors and of inhibitors of further disease-relevant target structures", filed Apr. 20, 2012, which claims the benefit of German Application No. 10 2011 106 984.8, entitled "Microarray device for the screening or finding of HSP90 inhibitors and of inhibitors of further disease-relevant target structures" filed Jul. 8, 2011, both of which are incorporated by reference herein in their entirety.

The present invention relates to a microarray device for the screening or the finding of protein inhibitors, to a method for the production thereof, and to a corresponding method for screening or finding protein inhibitors. The microarray device according to the invention comprises a solid supporting element having a support material, at least one protein immobilized thereon for which inhibitors are to be screened or found, and at least one known inhibitor of the at least one protein, the inhibitor being bound to the at least one protein and comprising a detectable label.

Biochips having immobilized nucleic acids, peptides or proteins, known as microarrays, are of great potential not only in basic biological and biochemical research, but also in areas of diagnostics or pharmacology, for example when searching for novel therapeutically relevant active ingredients. They allow the parallel analysis of up to thousands of individual detection events, for example binding reactions, in a small amount of biological sample material, and are therefore enjoying increasing popularity.

Microarrays normally consist of a solid supporting element or of a solid supporting element having a support material, for example treated or untreated glass or plastic, on which biological molecules are immobilized in hundreds or thousands of precisely defined positions, known as spots. Said spots can, in turn, be present in exactly defined arrangements, for example in multiple square fields of 10×10 spots. In the case of said arrangements, the biological molecules are applied to or "spotted" onto the supporting element or the support material by special printers. Said printers are capable of applying tiny droplets of solutions containing the biological molecules in defined patterns. When the biological molecules are immobilized on the supporting element or the support material, the microarray can be used.

Heat shock proteins (HSPs) are present in all cellular systems, and are essential in eukaryotes. Some HSPs, for example HSP90, are target structures for the development of cancer therapeutics and a starting point for the development of active ingredients against further severe diseases. HSP90 is a highly conserved protein which constitutes an important folding machine in the chaperone complex of the cell, by bringing unfolded or incorrectly folded proteins into the correct form. Therefore, said protein, which is induced only by cellular stress, has an important role in a range of disease processes. For example, investigations show that HSP90 occurs substantially more frequently in cancer cells than in normal cells. In this context, HSP90 expression is actually further enhanced in advanced tumors. If mutations in cancers lead to more unfolded proteins, then the HSP90 content of the cells concerned also increases. This prevents apoptosis of the cells, which is what is actually required and which would otherwise inevitably occur as a result of the accumulation of unfolded proteins. Thus, if the activity of HSP90 can be inhibited, for example by an HSP90 inhibitor, the cancer cell dies.

In addition to the HSPs, there is also additionally a multiplicity of further target structures for the development of therapeutically effective substances for the treatment of a multiplicity of syndromes, for example further chaperones, ion channels and receptors.

Tolerable and adverse effect-free inhibitors of HSP90 and of a multiplicity of further disease-relevant structures are thus of increased interest as active ingredients for the treatment of tumors and a multiplicity of further diseases. In this connection, numerous active ingredients have already been selected. Nevertheless, optimization and further development of the arsenal of active ingredients is necessary, since many of the active ingredients to date have considerable adverse effects or are increasingly limited in their use because of development of resistance.

In this connection, methods to date for screening such inhibitors, for example fluorescence polarization, total internal reflection fluorescence microscopy (TIRF) or the so-called Alphascreen® method, are very expensive and complicated, especially in the high-throughput field. Furthermore, it has not been possible to date to perform functional screening of protein inhibitors using conventional microarrays, since said microarrays were only capable of providing structural information. For instance, normally the detection of the binding of two binding partners is still not able to reveal anything about the functional consequences.

It is therefore an object of the present invention to provide means for the screening or finding of protein inhibitors, which means can be produced in a simple and cost-effective manner, has high sensitivity, consumes litle material, is easily standardizable, and is applicable to a multiplicity of possible target structures and diseases.

This object is achieved by the embodiments characterized in the claims. More particularly, the invention provides a microarray device for the screening or finding of protein inhibitors, a method for the production thereof, and a corresponding screening or finding method. In this regard, the microarray device according to the invention is notable for its simple and cost-effective production, high sensitivity and accuracy coupled with very low material consumption, good standardizability, and the property of being applicable in the case of a multiplicity of disease-relevant target structures.

Accordingly, the present invention provides a microarray device for the screening or finding of protein inhibitors, comprising:
(a) a solid supporting element having a support material,
(b) at least one protein for which inhibitors are to be screened or found, the protein being immobilized on the surface of the support material, and
(c) at least one known inhibitor of the at least one protein, the inhibitor being bound to the at least one protein and comprising a detectable label.

In this context, suitable solid supporting elements for use in microarray devices according to the invention are not subject to any special restrictions whatsoever and are known in the prior art. For example, it is possible to use conventional glass, plastic and silicone slides. Furthermore, it is possible to use supporting elements having glass and/or metal surfaces, for example gold surfaces. However, according to the invention, it is also possible to use nonwoven-type materials such as paper or cardboard. The supporting elements can be coated with a support material, for example with nitrocellulose, or with multilayer support materials, such as nitrocellulose and metal, for example a metallized support material containing nitrocellulose. In this case, the metal not only acts as a support material, but also simultaneously serves as a reflective layer for signal intensification. With regard to the support material, the nitrocellulose can be porous or unporous. If the support materials are porous, the microarray devices according to the invention can be operated in lateral flow. Commercially available, nitrocellulose-coated glass supports for use in microarrays are, for example, sold by Schott under the name "Nexterion® Slide NC-N" and by Avantra Biosciences Corp. under the name "Path Slide".

The protein immobilized on the microarray device according to the invention is preferably a protein which constitutes a disease-relevant target structure, i.e., the inhibition thereof is or might be of demonstrated or suspected therapeutic use. Preferably, the protein is selected from the group consisting of chaperones, including heat shock proteins (HSPs), ion channels and receptors. Particularly preferably, the protein is HSP90, very particularly preferably human HSP90. Further preferred proteins are bacterial heat shock proteins such as the so-called HtpG proteins, which occur in disease-relevant pathogens such as, for example, *Helicobacter pylori, Helicobacter hepaticus, Mycobacterium tuberculosum, Mycobacterium leprae, Mycobacterium bovis,* and *Escherichia coli,* heat shock proteins of the malaria parasites from the genus *Plasmodium* or of parasites such as *Schistosoma mansoni* or *Leishmania* sp., or animal and plant HSPS. The immobilized protein is covalently or adsorptively immobilized on the microarray device according to the invention, and is preferably a full-length native protein, though it is also possible to use protein fragments provided that they contain the binding site for the known inhibitor in its native configuration. Furthermore, preference is given to using highly purified proteins.

Methods for preparing recombinant proteins for use in the microarray device according to the invention are known in the prior art. For example, they comprise the expression of the proteins in bacterial or eukaryotic systems (e.g., in *E. coli,* mammalian cells or insect cells), and the subsequent purification of the proteins.

The known inhibitor of the protein immobilized on the microarray device according to the invention is likewise not subject to any special restrictions whatsoever. More particularly, for a multiplicity of relevant proteins, inhibitors are known in the prior art. They can be other proteins, peptides or organic compounds. The inhibitor is present on the microarray device according to the invention bound to the immobilized protein on its native binding site, and comprises a detectable label.

In one embodiment of the microarray device according to the invention, any labeled ligand of the immobilized protein can be used instead of known inhibitors. This way, it is also possible to investigate unknown binding sites on the immobilized protein, or substances binding thereto.

In embodiments in which the immobilized protein is HSP90, the known inhibitor is preferably selected from the group consisting of geldanamycin, a benzoquinoid ansamycin from *Streptomyces hygroscopicus,* geldanamycin analogs and geldanamycin derivatives. In this case, particular preference is given to 17-allylamino-17-demethoxygeldanamycin (17-AAG).

The detectable label of the known inhibitor is likewise not subject to any special restrictions. More particularly, suitable labels are known in the prior art. They preferably comprise fluorescent dyes, a particularly preferred fluorescent dye being fluorescein isothiocyanate (FITC). Furthermore, biotin can be used as a label, and methods for labeling the inhibitors with a suitable detectable label are known in the prior art.

In a preferred embodiment, the microarray device according to the invention comprises at least one or more further proteins for which inhibitors are to be screened. In this case, the various proteins are immobilized in different and distinguishable regions of the solid support material. The number of different proteins immobilized on a microarray device according to the invention is in this case only limited by the number of distinguishable regions on the solid support material. The further proteins are preferably proteins as defined above for the at least one protein.

In a further preferred embodiment, the microarray device according to the invention comprises at least one or more further known inhibitors of the at least one protein. They are likewise bound to their native binding site on the protein and comprise a detectable label. In this case, the detectable labels of the different inhibitors are distinguishable from one another. Furthermore, the different inhibitors are bound to the protein at different binding sites. The number of different inhibitors is thus only limited by the number of binding sites for inhibitors on the protein. The further inhibitors are preferably inhibitors as defined above for the at least one inhibitor.

The present invention further provides a method for producing the microarray device according to the invention, comprising the steps of:
(a) providing a suitable solid supporting element having a support material,
(b) immobilizing on the surface of the support material at least one protein for which inhibitors are to be screened, and
(c) binding at least one known inhibitor of the at least one protein to the at least one protein, the inhibitor comprising a detectable label.

In said method, the solid supporting element, the support material, the at least one protein, further proteins optionally present, the at least one known inhibitor, further inhibitors optionally present, and the detectable label are as defined above.

Methods for immobilizing proteins on solid support materials are known in the prior art and comprise, for example, spotting a solution containing the protein to be immobilized onto the solid support material using a suitable printer. Methods for labeling the inhibitor with a suitable detectable label are likewise known in the prior art. Furthermore, methods for binding the inhibitor to the at least one protein are known. They comprise, for example, the incubation of the microarray device on which protein is already immobilized with a solution containing the labeled inhibitor.

When using the microarray device according to the invention, the microarray device is incubated with one or more test solutions suspected of containing an inhibitor for the immobilized protein. If the test solutions contain substances which bind more strongly to the immobilized protein than the known and labeled inhibitor bound thereto, said inhibitor is displaced from the immobilized protein. If the test solutions contain substances exhibiting a comparable binding interaction, they will displace the immobilized inhibitor from the immobilized proteins in a competitive manner because of their high free concentration. Both are detectable through a decrease in the signal produced by the detectable label. Thus, it is possible to infer from a decrease in the signal produced by the detectable label on a particular site of the microarray device according to the invention that the test solution present at said site contains an inhibitor which binds to the same binding site as the known inhibitor.

Accordingly, the present invention further provides a method for screening or finding protein inhibitors, comprising the steps of:
(a) providing a microarray device according to the invention,
(b) determining the intensities of the signals produced by the detectable label bound on the microarray device,
(c) incubating the microarray device with one or more test solutions to be screened or to be searched through,
(d) determining again the intensities of the signals produced by the detectable label bound on the microarray device, and
(e) determining whether a test solution contained a protein inhibitor, this being the case if the intensities determined in step (d) are smaller than the intensities determined in step (b).

In said method, methods for determining the intensities of the signals produced by the detectable label bound on the microarray device are known in the prior art. They comprise, for example, scanning of the microarray device using a conventional microarray scanner in the case of use of fluorescent dyes as detectable label.

In the figures:

FIG. 1: shows a diagram of a microarray device according to the invention having immobilized HSP90 and FITC-labeled geldanamycin as inhibitor. (A) The microarray substrate consists of a glass support containing 16 nitrocellulose pads. (B) Detailed view of one nitrocellulose pad. HSP90 is printed in 10 replicates on each pad. Theoretically, a print with 10×10 spots is possible. (C) Principle behind the displacement assay. Firstly, FITC-labeled geldanamycin is bound to the immobilized HSP90. It can be displaced by an inhibitor having the same binding site as geldanamycin. The displacement results in a decrease in fluorescence intensity.

Figure 2:
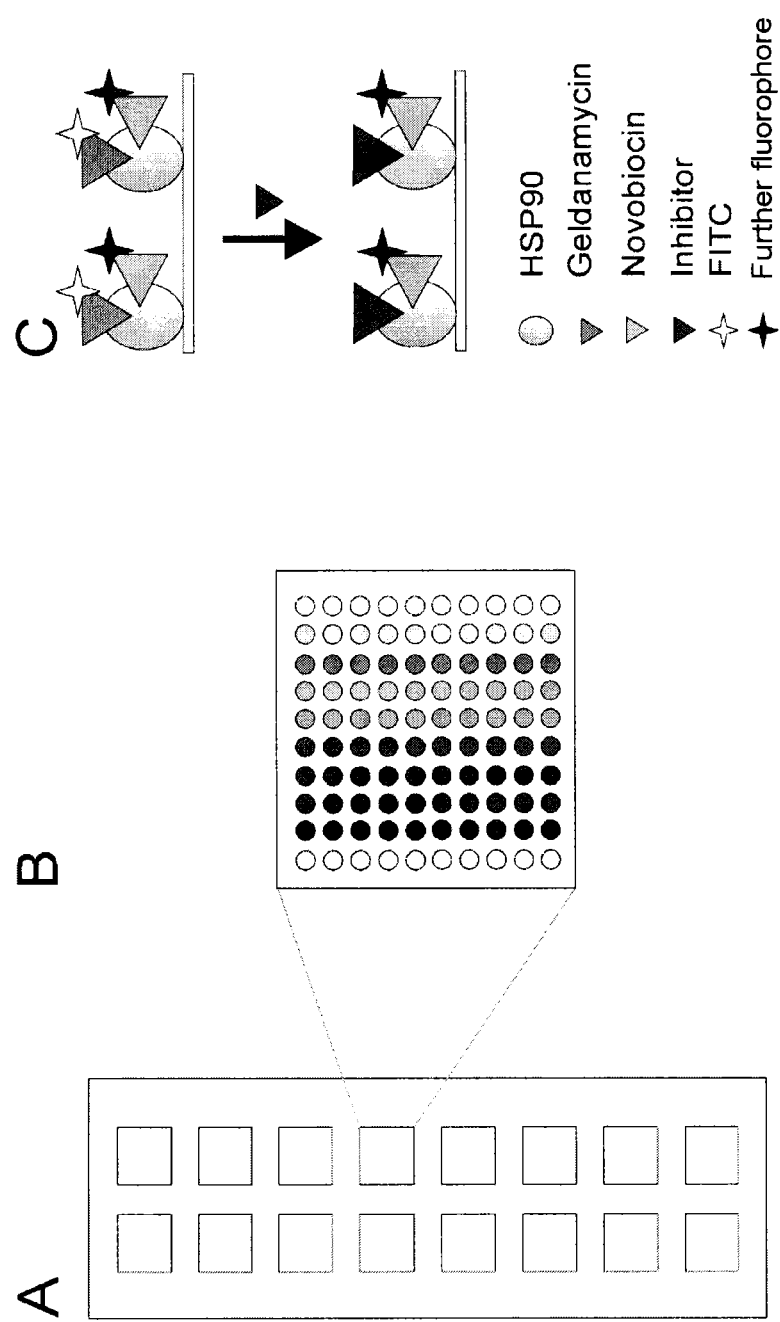

FIG. 2: shows a diagram of a microarray device according to the invention having a plurality of different immobilized proteins and a plurality of different inhibitors. (A) The microarray substrate consists of a glass support containing 16 nitrocellulose pads. (B) The microarray provides the possibility of immobilizing a plurality of different proteins (multiplexing at the target level). For instance, it is possible to investigate the effect of one potential inhibitor on the different proteins. (C) In addition, there is also the possibility of using a plurality of different known inhibitors (multiplexing at the inhibitor level). For instance, it is possible to use, for example, not only FITC-labeled geldanamycin but also novobiocin labeled with a different fluorophore. In this case, novobiocin binds to a position on HSP90 different to that for geldanamycin, but also results in inhibition of HSP90 activity. Thus, it is possible to investigate multiple possible target points on HSP90 on a single microarray. In the situation depicted, the inhibitor displaces the geldanamycin, whereas the binding of the novobiocin is not affected.

Figure 3:
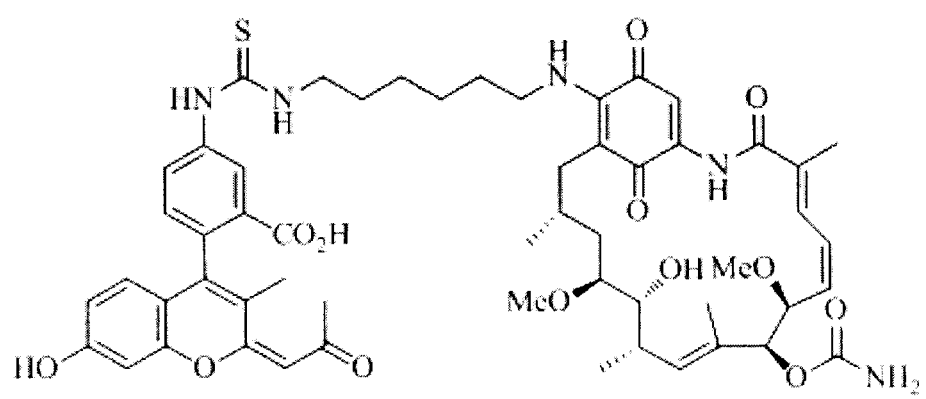

FIG. 3: shows the structural formula of FITC-labeled geldanamycin.

The present invention will now be more particularly elucidated with reference to the following nonrestricting examples.

EXAMPLE 1

Production of a Microarray Device According to the Invention

The microarrays were printed on nitrocellulose-coated 16-pad slides (Nexterion® Slide NC-N16; Schott, Mainz, Germany). A contactless printer (Nano-Plotter NP 2.1; Gesim, Grosserkmannsdorf, Germany) and a Nano-Tip A (Gesim) were used for printing.

The target (HSP90) was initially charged in buffer A (20 mM Tris, 50 mM KCl, 6 mM mercaptoethanol, 10% glycerol, pH 7.5) in a concentration of 3 mg/ml. Prior to spotting, 10% of a 5% strength trehalose solution were added to the target solution (final protein concentration: 2.73 mg/ml, final trehalose concentration: 0.5%). Thereafter, the target solution was printed onto the slide. During printing, 8 droplets were spotted per spot. Each target solution is printed in 10 replicates on each of the 16 fields of the microarray. Subsequently, the microarray was incubated at room temperature for 30 min, then blocked in 1% BSA in buffer A at room temperature for 45 min with agitation, and then washed for 3×20 min with buffer A at room temperature with agitation.

Thereafter, the microarray was incubated at 4° C. overnight (16 to 18 h) with 3 ml of a solution of 15 nM FITC-labeled geldanamycin in buffer B (20 mM HEPES-KOH, 50 mM KCl, 5 mM $MgCl_2$, 20 mM $Na_2MoO_4$, 1 mM DTT, 0.01% Tween 20, 2% DMSO, 0.1 mg/mL BSA, pH 7.3) away from light and with agitation. Subsequently, the microarray was washed three times, each time with 3 ml of buffer B for 20 min, away from light and with agitation and then dried under pressurized air.

EXAMPLE 2

Use of a Microarray Device According to the Invention

The microarray was scanned using a GenePix 4000B scanner (Molecular Devices, Ismaning, Germany) in the Cy3 channel. For the scanning operation, the laser power was reduced to 33%, and the gain was selected such that clear, but not saturated, signals were obtained (gain 250-gain 350).

Subsequently, a self-adhesive 16-pad hybridization chamber (Nexterion® 16 Well Superstructures; Schott) was applied to the microarray. The 16 wells of the hybridization chamber were then filled with the potential inhibitors under investigation.

In said chamber, 50 µl of the substance in buffer B were used per well. To acquire a displacement curve, concentrations between 0.25 µM and 2.5 µM were used. One well was filled with 2.5 µM 17-AAG as positive control, and a further well was filled with buffer B as negative control. The hybridization chamber was sealed with film and the microarray was placed in a humid chamber. Incubation with the inhibitors was carried out at 4° C. overnight (16 to 18 h) with agitation and away from light.

Thereafter, the film was removed from the hybridization chamber and the solution was removed from the individual wells. Each of the wells was washed three times, each time with 100 µl of buffer B for 5 min. Then, the hybridization chamber was removed and the microarray was dried under pressurized air.

Subsequently, the microarray was scanned using the same scanner settings which were also used following the incubation with FITC-labeled geldanamycin.

Raw analysis was carried out by quantifying the mean signal intensity (e.g., by means of ImaGene or GenePix Pro; Molecular Devices). In said analysis, both the scan after incubation with FITC-labeled geldanamycin and the scan after incubation with the potential inhibitors were analyzed. Thus, each spot yielded two mean signal intensities. Calculating the difference from said signal intensities yielded the displaced signal. Mean values and standard deviations were obtained by analyzing 10 replicates in each case, and IC$_{50}$ values were determined via displacement curves, for example by means of Origin (OriginLab, Northampton, USA).

The invention claimed is:

1. A microarray device for the screening or finding of protein inhibitors, comprising:
    (a) a solid supporting element having a support material,
    (b) at least one protein for which inhibitors are to be screened or found, the protein being immobilized on the surface of the support material, and
    (c) at least one known inhibitor of the at least one protein, the inhibitor being bound to the at least one protein and comprising a detectable label; and at least one further known inhibitor of the at least one protein, wherein the further known inhibitor is different from the at least one known inhibitor, is bound to the at least one protein at a different binding site from the at least one known inhibitor, and comprises a detectable label, the detectable labels of the at least one known inhibitor and the further known inhibitor being distinguishable from one another.

2. The microarray device as claimed in claim 1, wherein the solid supporting element consists of paper or cardboard.

3. The microarray device as claimed in claim 1, wherein the support material is nitrocellulose.

4. The microarray device as claimed in claim 1, wherein the support material is metallized and contains nitrocellulose.

5. The microarray device as claimed in claim 1, wherein the at least one protein is selected from the group consisting of heat shock proteins (HSPs), chaperones, ion channels and receptors.

6. The microarray device as claimed in claim 5, wherein the at least one protein is HSP90.

7. The microarray device as claimed in claim 1, wherein the at least one known inhibitor is selected from the group consisting of proteins, peptides and organic compounds.

8. The microarray device as claimed in claim 6, wherein the at least one known inhibitor of HSP90 is selected from the group consisting of geldanamycin, geldanamycin analogs and geldanamycin derivatives.

9. The microarray device as claimed in claim 8, wherein the at least one known inhibitor of HSP90 is 17-allylamino-17-demethoxygeldanamycin (17-AAG).

10. The microarray device as claimed in claim 1, wherein the detectable label is a fluorescent dye.

11. The microarray device as claimed in claim 10, wherein the fluorescent dye is fluorescein isothiocyanate (FITC).

12. The microarray device as claimed in claim 1, wherein the microarray device comprises at least one further protein for which inhibitors are to be screened or found, the different proteins being immobilized in different regions on the surface of the support material.

13. A method for producing the microarray device as claimed in claim 1, comprising the steps of:
    (a) providing a suitable solid supporting element having a support material,
    (b) immobilizing on the surface of the support material at least one protein for which inhibitors are to be screened, and
    (c) binding at least one known inhibitor of the at least one protein to the at least one protein, the inhibitor comprising a detectable label; and
    (d) binding at least one further known inhibitor of the at least one protein to the at least one protein, wherein the further known inhibitor is different from the at least one known inhibitor, is bound to the at least one protein at a different binding site from the at least one known inhibitor, and comprises a detectable label, the detectable labels of the at least one known inhibitor and the further known inhibitor being distinguishable from one another.

14. A method for screening protein inhibitors, comprising the steps of:
    (a) providing a microarray device as claimed in claim 1,
    (b) determining the intensities of the signals produced by any detectable label bound on the microarray device,
    (c) incubating the microarray device with one or more test solutions to be screened or to be searched through,
    (d) determining again the intensities of the signals produced by any detectable label bound on the microarray device, and
    (e) determining whether a test solution contained a protein inhibitor, this being the case if the intensities determined in step (d) are smaller than the intensities determined in step (b).

* * * * *